United States Patent
Park et al.

(10) Patent No.: US 12,014,502 B2
(45) Date of Patent: Jun. 18, 2024

(54) METHOD AND DEVICE FOR EVALUATING QUALITY OF PATHOLOGICAL SLIDE IMAGE

(71) Applicant: Lunit Inc., Seoul (KR)

(72) Inventors: Ga Hee Park, Seoul (KR); Kyung Hyun Paeng, Seoul (KR); Chan Young Ock, Seoul (KR); Sang Hoon Song, Anseong-si (KR); Suk Jun Kim, Seoul (KR)

(73) Assignee: Lunit Inc., Seoul (KR)

( * ) Notice: Subject to any disclaimer, the term of this patent is extended or adjusted under 35 U.S.C. 154(b) by 0 days.

(21) Appl. No.: 18/321,132

(22) Filed: May 22, 2023

(65) Prior Publication Data

US 2023/0386028 A1  Nov. 30, 2023

(30) Foreign Application Priority Data

May 24, 2022 (KR) .......... 10-2022-0063320
Mar. 23, 2023 (KR) .......... 10-2023-0038276

(51) Int. Cl.
| G06K 9/00 | (2022.01) |
| G06T 7/00 | (2017.01) |
| G06V 20/69 | (2022.01) |
| G16H 15/00 | (2018.01) |
| G16H 30/40 | (2018.01) |

(52) U.S. Cl.
CPC .......... *G06T 7/0012* (2013.01); *G06V 20/698* (2022.01); *G16H 15/00* (2018.01); *G16H 30/40* (2018.01); *G06T 2207/30024* (2013.01); *G06T 2207/30096* (2013.01); *G06T 2207/30168* (2013.01); *G06T 2207/30204* (2013.01); *G06V 2201/03* (2022.01)

(58) Field of Classification Search
None
See application file for complete search history.

(56) References Cited

U.S. PATENT DOCUMENTS

| 2020/0272864 A1* | 8/2020 | Faust .................. G06V 10/764 |
| 2021/0398278 A1* | 12/2021 | Locke .................. G06T 7/194 |
| 2022/0036971 A1 | 2/2022 | Yoo et al. |
| 2022/0237788 A1* | 7/2022 | Shaul .................. G06V 20/698 |

FOREIGN PATENT DOCUMENTS

| JP | 2000-126182 A | 5/2000 |
| KR | 10-2016-0062358 A | 6/2016 |
| KR | 10-2020-0073305 A | 6/2020 |
| KR | 10-2021-0145778 A | 12/2021 |

(Continued)

OTHER PUBLICATIONS

Korean Office Action dated Jun. 21, 2023 in Korean Application No. 10-2023-0038276.

(Continued)

*Primary Examiner* — Wei Wen Yang
(74) *Attorney, Agent, or Firm* — Sughrue Mion, PLLC

(57) ABSTRACT

A computing device includes at least one memory, and at least one processor configured to analyze at least one object expressed in a pathological slide image, evaluate quality of the pathological slide image based on a result of the analyzing, and perform at least one additional operation according to a result of the evaluating.

17 Claims, 14 Drawing Sheets

(56) References Cited

FOREIGN PATENT DOCUMENTS

| WO | WO-2019108888 A1 * | 6/2019 | ........... G06K 9/0014 |
| WO | 2021/141757 A1 | 7/2021 | |

OTHER PUBLICATIONS

V. Azimi et al., "Breast Cancer Histopathology Image Analysis Pipeline for Tumor Purity Estimation", IEEE, 2017, 1137-1140 (4 pages total).
Communication issued in the European Patent Office in corresponding EP Application No. 23174891.4 dated Aug. 17, 2023.
Korean Office Action dated Mar. 22, 2024 in App. No. 10-2023-0038276.

* cited by examiner

METHOD AND DEVICE FOR EVALUATING QUALITY OF PATHOLOGICAL SLIDE IMAGE

CROSS-REFERENCE TO RELATED APPLICATION

This application is based on and claims priority under 35 U.S.C. § 119 to Korean Patent Applications No. 10-2022-0063320, filed on May 24, 2022, and No. 10-2023-0038276, filed on Mar. 23, 2023, in the Korean Intellectual Property Office, the disclosures of which are incorporated by reference herein in their entireties.

BACKGROUND

1. Field

The present disclosure relates to a method and device for evaluating the quality of a pathological slide image.

2. Description of the Related Art

Digital pathology is a field for obtaining histological information of a patient or predicting a prognosis by using a whole slide image generated by scanning a pathological slide image.

The pathological slide image may be obtained from a stained tissue sample of an object. For example, a tissue sample may be stained by various staining methods, such as hematoxylin and eosin, trichrome, periodic acid-Schiff, autoradiography, enzyme histochemistry, immunofluorescence, and immunohistochemistry. The stained tissue sample may be used for histology and biopsy evaluations, and thus may operate as a basis for determining whether to move on to molecular profile analysis to understand a disease state.

However, there is a limit in that diagnosis by a pathologist or a doctor through a pathological slide image may not produce an accurate result because subjective judgment is highly likely to affect the diagnosis.

SUMMARY

Provided a method and device for evaluating the quality of a pathological slide image. Provided is a computer-readable recording medium having recorded thereon a program for causing a computer to execute the method. The objectives of the present disclosure are not limited to those described above, and other objectives may be obtained.

Additional aspects will be set forth in part in the description which follows and, in part, will be apparent from the description, or may be learned by practice of the presented embodiments of the disclosure.

According to an aspect of an embodiment, a computing device includes at least one memory, and at least one processor configured to analyze at least one object expressed in a pathological slide image, evaluate quality of the pathological slide image based on a result of the analyzing, and perform at least one additional operation according to a result of the evaluating.

According to an aspect of another embodiment, a method of evaluating a pathological slide image includes analyzing at least one object expressed in the pathological slide image, evaluating quality of the pathological slide image based on a result of the analyzing, and performing at least one additional operation according to a result of the evaluating.

According to an aspect of another embodiment, a non-transitory computer-readable recording medium includes a recording medium recording thereon a program for causing a computer to execute the above-described method.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 8 is a diagram illustrating an example of a screen displayed by a processor according to an embodiment;

FIGS. 11A to 11C are diagrams for describing examples of modifying information related to a pathological slide image, according to an embodiment.

DETAILED DESCRIPTION

Figure 1:
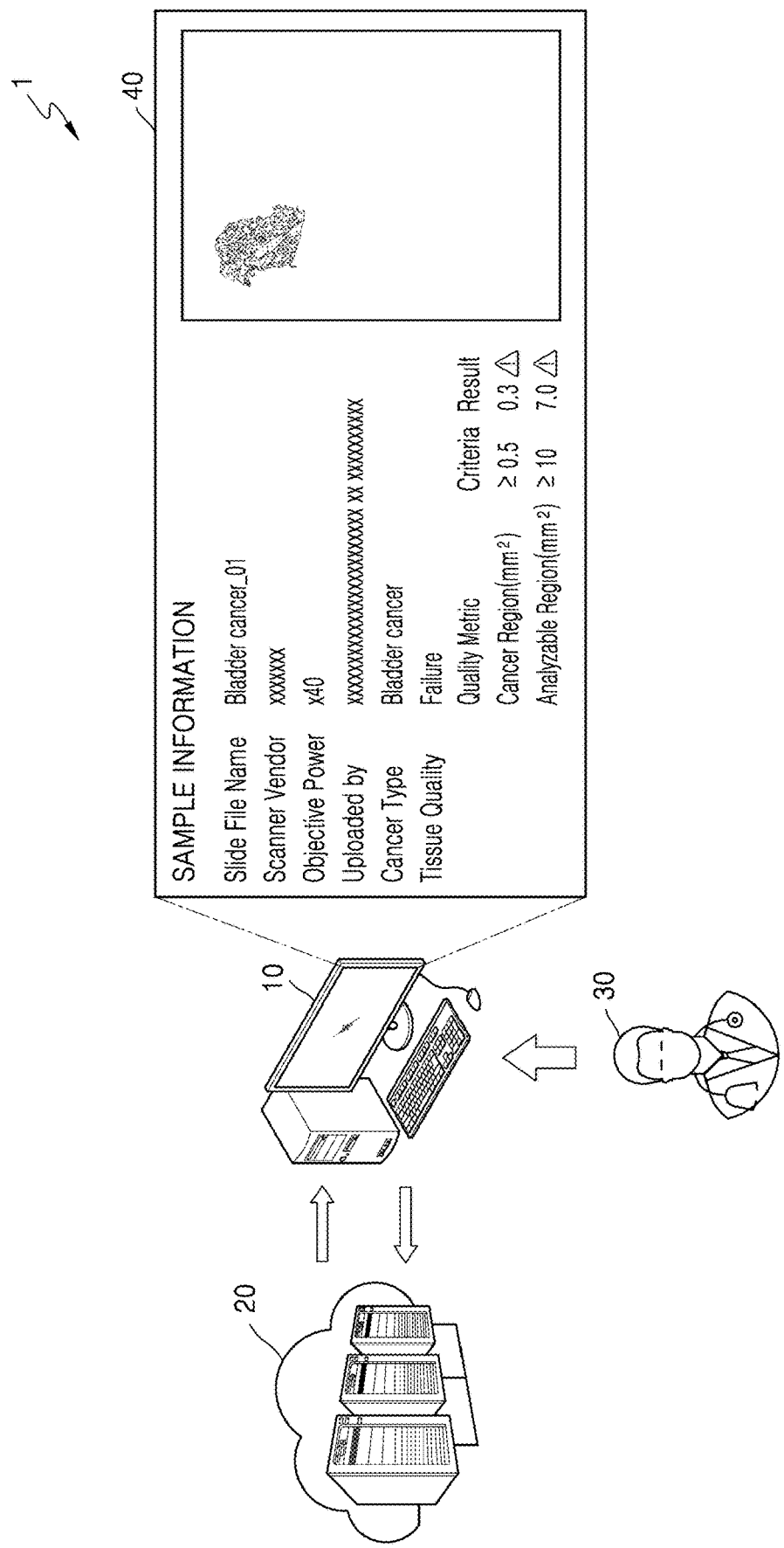
FIG. 1 is a diagram for describing an example of a system for evaluating a pathological slide image according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Terms used in embodiments are selected as currently widely used general terms as possible, which may vary depending on intentions or precedents of one of ordinary skill in the art, emergence of new technologies, and the like. In addition, in certain cases, there are also terms arbitrarily selected by the applicant, and in this case, the meaning thereof will be defined in detail in the description. Therefore, the terms used herein should be defined based on the meanings of the terms and the details throughout the present description, rather than the simple names of the terms.

Throughout the present specification, when a part "includes" a component, it means that the part may additionally include other components rather than excluding other components as long as there is no particular opposing recitation. In addition, the term, such as " . . . unit" or " . . . module" described herein, refers to a unit that processes at least one function or operation, which may be implemented as hardware or software, or a combination of hardware and software.

In addition, although the terms such as "first" or "second" may be used herein to describe various elements, these elements should not be limited by these terms. These terms may be only used to distinguish one element from another.

According to an embodiment, a "pathological slide image" may refer to an image obtained by photographing a pathological slide that is fixed and stained via a series of chemical treatment processes for tissue or the like removed from a human body. In addition, the pathological slide image may refer to a whole slide image (WSI) including a high-resolution image of a whole slide, and may also refer to a portion of the whole slide image, for example, one or more patches. For example, the pathological slide image may refer to a digital image captured or scanned via a scanning apparatus (e.g., a digital scanner or the like), and may include information about a particular protein, cell, tissue, and/or structure within a human body. In addition, the pathological slide image may include one or more patches, and histological information may be applied (e.g., tagged) to the one or more patches via an annotation operation.

According to an embodiment, the term "medical information" may refer to any medically meaningful information that may be extracted from a medical image, and may include, for example, the region, position, and size of a particular tissue (e.g., a cancer tissue or a cancer stroma tissue) and/or a particular cell (e.g., a tumor cell, a lymphocyte, a macrophage, an endothelial cell, or a fibroblast) in a medical image, diagnostic information regarding cancer, information associated with a subject's possibility of developing cancer, and/or a medical conclusion associated with cancer treatment, but is not limited thereto. In addition, the medical information may include not only a quantified numerical value that may be obtained from a medical image, but also information obtained by visualizing the numerical value, predictive information according to the numerical value, image information, statistical information, and the like. The medical information generated as described above may be provided to a user terminal or output or transmitted to a display device to be displayed.

Hereinafter, embodiments will be described in detail with reference to the accompanying drawings. The embodiments may, however, be embodied in many different forms and should not be construed as being limited to the embodiments set forth herein.

FIG. 1 is a diagram for describing an example of a system for evaluating a pathological slide image according to an embodiment.

Referring to FIG. 1, a system 1 includes a user terminal 10 and a server 20. For example, the user terminal 10 and the server 20 may be connected to each other by a wired or wireless communication method to transmit and/or receive data (e.g., image data or the like) to and/or from each other.

For convenience of description, FIG. 1 illustrates that the system 1 includes the user terminal 10 and the server 20, but the present disclosure is not limited thereto. For example, other external devices (not shown) may be included in the system 1, and operations of the user terminal 10 and the server 20 to be described below may be implemented by a single device (e.g., the user terminal 10 or the server 20) or more devices.

The user terminal 10 may be a computing device including a display device and a device (e.g., a keyboard, a mouse, or the like) for receiving a user input, and includes a memory and a processor. For example, the user terminal 10 may correspond to a notebook personal computer (PC), a desktop PC, a laptop, a tablet computer, a smart phone, or the like, but is not limited thereto.

The server 20 may be a device that communicates with an external device such as the user terminal 10. For example, the server 20 may be a device that stores various types of data including a pathological slide image, a bitmap image corresponding to the pathological slide image, information generated by analyzing the pathological slide image (including, for example, information about at least one tissue and cell expressed in the pathological slide image, at least one piece of biomarker expression information, and the like), and information about a machine learning model used for analyzing the pathological slide image. The server 20 may be a computing device including a memory and a processor, and having a computing capability. In a case in which the server 20 is a computing device, the server 20 may perform at least some of operations of the user terminal 10 to be described below with reference to FIGS. 1 to 11C. For example, the server 20 may also be a cloud server, but is not limited thereto.

The user terminal 10 outputs an image 40 representing information generated through analysis of a pathological slide image and/or a pathological slide. For example, various pieces of information about at least one tissue and cell expressed in the pathological slide image may be expressed in the image 40. In addition, biomarker expression information may be expressed in the image 40. In addition, the image 40 may be a report including medical information about at least some regions included in the pathological slide image. Also, the image 40 may be a report including a result of evaluating the pathological slide image.

The pathological slide image may refer to an image obtained by photographing a pathological slide that is fixed and stained through a series of chemical treatment processes in order to observe, with a microscope, a tissue or the like removed from a human body. For example, the pathological slide image may refer to a whole slide image including a high-resolution image of a whole slide. As another example, the pathological slide image may refer to a part of the high-resolution whole slide image.

In addition, the pathological slide image may refer to a patch region obtained by dividing the whole slide image into patch units. For example, the patch may have a size of a certain region. Alternatively, the patch may refer to a region including each of objects included in the whole slide.

In addition, the pathological slide image may refer to a digital image captured by using a microscope, and may include information about cells, tissues, and/or structures in the human body.

Biological elements (e.g., cancer cells, immune cells, cancer regions, etc.) expressed in the pathological slide image may be identified by analyzing the pathological slide image. These biological elements may be used for histological diagnosis of a disease, prognosis of a disease, determination of a therapeutic direction for a disease, and the like.

Meanwhile, analysis of the pathological slide image by a user 30 may include subjective judgment by the user 30, and thus, it may be difficult to objectively diagnose the subject. As a solution to this issue, a tool for analyzing a pathological slide image by using a machine learning model have been developed. However, in a case in which the quality of the pathological slide image is not guaranteed, the accuracy of a result output through the machine learning model may decrease. In detail, because a standard format for pathological slide images has not been established, potential bias may be included in downstream analysis of a pathological slide image through the machine learning model.

The user terminal 10 according to an embodiment analyzes at least one object represented in the pathological slide image, and evaluates the quality of the pathological slide image based on a result of the analyzing. Then, the user terminal 10 performs at least one additional operation according to the result of the evaluating.

Accordingly, the user 30 may check a result of quality evaluation of the pathological slide image, and the accuracy of downstream analysis of the pathological slide image may be improved. Furthermore, an evaluation method according to an embodiment may be provided as a standard method for managing the quality of a pathological slide image, and standardization of machine learning models for workflows of digital pathology may be established.

Hereinafter, an example in which the user terminal 10 analyzes a pathological slide image, evaluates the quality of the pathological slide image based on a result of the analyzing, and performs at least one additional operation according to a result of the evaluating will be described with reference to FIGS. 2 to 11C.

Meanwhile, for convenience of description, it is described herein that the user terminal 10 performs operations according to an embodiment, but the present disclosure is not limited thereto. For example, at least some of operations performed by the user terminal 10 may also be performed by the server 20.

In other words, at least some of operations of the user terminal 10 described with reference to FIGS. 1 to 11C may be performed by the server 20. For example, the server 20 may analyze tissues and cells expressed in the pathological slide image. In addition, the server 20 may evaluate the quality of the pathological slide image based on a result of the analyzing. In addition, the server 20 may perform at least one additional operation according to a result of the evaluating. In addition, the server 20 may transmit, to the user terminal 10, results of the analyzing, the evaluating, and/or the performing of the additional operation. However, the operation of the server 20 is not limited to the above.

Figure 2:
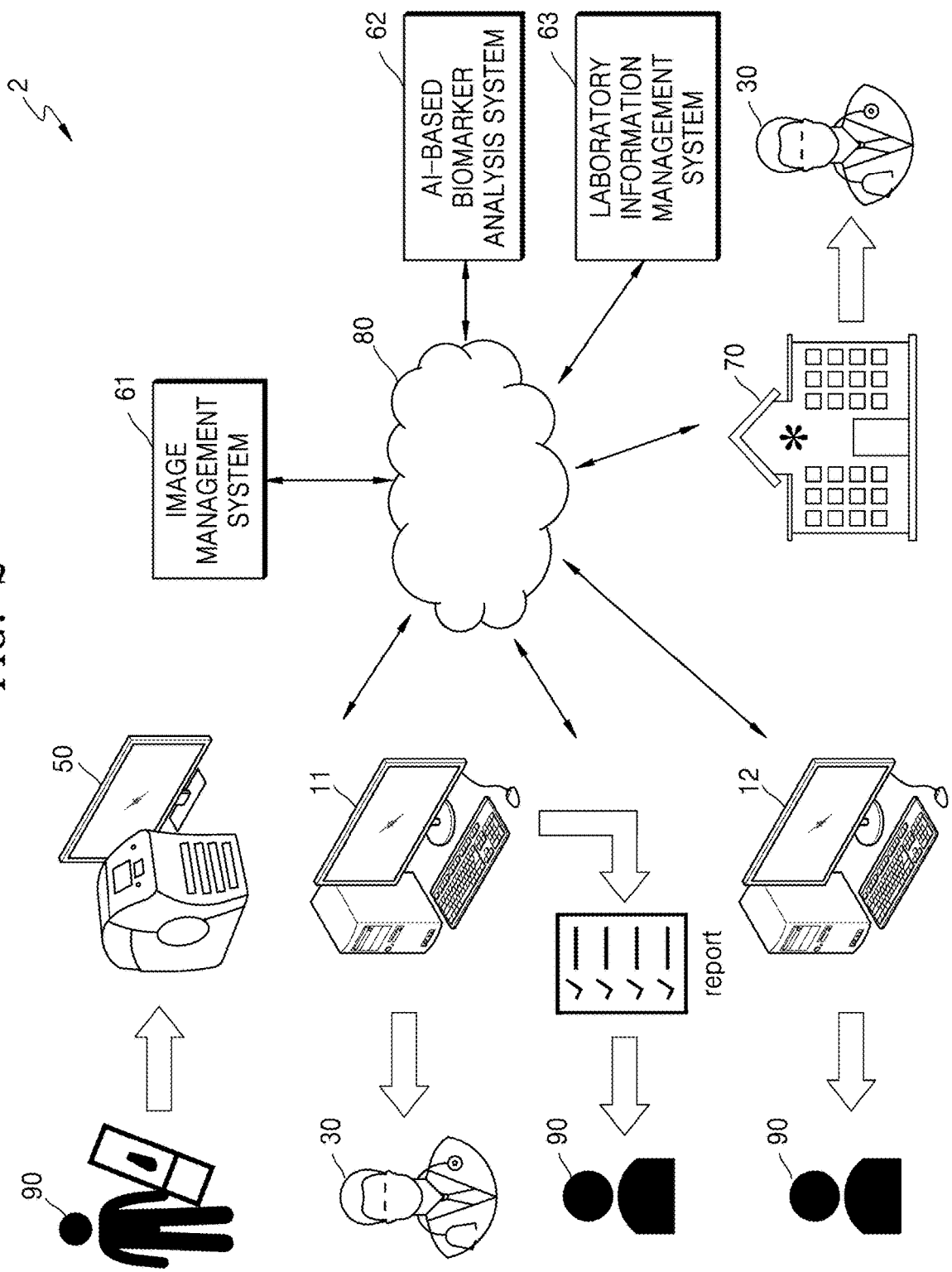
FIG. 2 is a block diagram of a system and a network for preparing, processing, and reviewing slide images of tissue specimens by using a machine learning model, according to an embodiment.

FIG. 2 is a block diagram of a system and a network for preparing, processing, and reviewing slide images of tissue specimens by using a machine learning model, according to an embodiment.

Referring to FIG. 2, a system 2 includes user terminals 11 and 12, a scanner 50, an image management system 61, an artificial intelligence (AI)-based biomarker analysis system 62, a laboratory information management system 63, and a server 70. In addition, the components (11, 12, 50, 61, 62, 63, and 70) included in the system 2 may be connected to each other through a network 80. For example, the network 80 may be a network through which the components (11, 12, 50, 61, 62, 63, and 70) may be connected to each other by a wired or wireless communication method. For example, the system 2 illustrated in FIG. 2 may include a network that may be connected to servers in hospitals, research facilities, laboratories, and the like, and/or user terminals of doctors or researchers.

According to various embodiments of the present disclosure, methods to be described below with reference to FIGS. 3A to 11C may be performed by the user terminals 11 and 12, the image management system 61, the AI-based biomarker analysis system 62, the laboratory information management system 63, and/or the hospital or laboratory server 70.

The scanner 50 may obtain a digitized image from a tissue sample slide generated by using a tissue sample of a subject 90. For example, the scanner 50, the user terminals 11 and 12, the image management system 61, the AI-based biomarker analysis system 62, the laboratory information management system 63, and/or the hospital or laboratory server 70 may be connected to the network 80, such as the Internet, through one or more computers, servers, and/or mobile devices, respectively, or may communicate with the user 30 and/or the subject 90 through one or more computers, and/or mobile devices.

The user terminals 11 and 12, the image management system 61, the AI-based biomarker analysis system 62, the laboratory information management system 63, and/or the hospital or laboratory server 70 may generate or otherwise obtain, from another device, one or more tissue samples of the subject 90, a tissue sample slide, digitized images of the tissue sample slide, or any combination thereof. In addition, the user terminals 11 and 12, the image management system 61, the AI-based biomarker analysis system 62, and the laboratory information management system 63 may obtain any combination of pieces of subject-specific information, such as age, medical history, cancer treatment history, family history, and past biopsy records of the subject 90, or disease information of the subject 90.

The scanner 50, the user terminals 11 and 12, the image management system 61, the laboratory information management system 63, and/or the hospital or laboratory server 70 may transmit digitized slide images and/or subject-specific information to the AI-based biomarker analysis system 62 through the network 80. The AI-based biomarker analysis system 62 may include one or more storage devices (not shown) for storing received images and data. In addition, the AI-based biomarker analysis system 62 may include a machine learning model repository that stores a machine learning model trained to process the received images and data. For example, the AI-based biomarker analysis system 62 may include a machine learning model that is trained to predict, from a pathological slide image of the subject 90, at least one of information about at least one cell, information about at least one region, information related to a biomarker, medical diagnostic information, and/or medical treatment information.

The scanner 50, the user terminals 11 and 12, the AI-based biomarker analysis system 62, the laboratory information management system 63, and/or the hospital or laboratory server 70 may transmit, to the image management system 61 through the network 80, a digitized slide image, subject-specific information, and/or a result of analyzing the digitized slide image. The image management system 61 may include a repository for storing received images and a repository for storing analysis results.

In addition, according to various embodiments of the present disclosure, a machine learning model that is trained to predict, from a slide image of the subject 90, at least one of information about at least one cell, information about at least one region, information related to a biomarker, medical diagnostic information, and/or medical treatment information, may be stored in the user terminals 11 and 12 and/or the image management system 61 and operate.

According to various embodiments of the present disclosure, a method of analyzing a pathological slide image, a method of processing subject information, a method of selecting a subject group, a method of designing a clinical trial, a method of generating biomarker expression information, and/or a method of setting a reference value for a particular biomarker may be performed not only by the AI-based biomarker analysis system 62, but also by the user terminals 11 and 12, the image management system 61, the laboratory information management system 63, and/or the hospital or laboratory server 70.

Figure 3A:
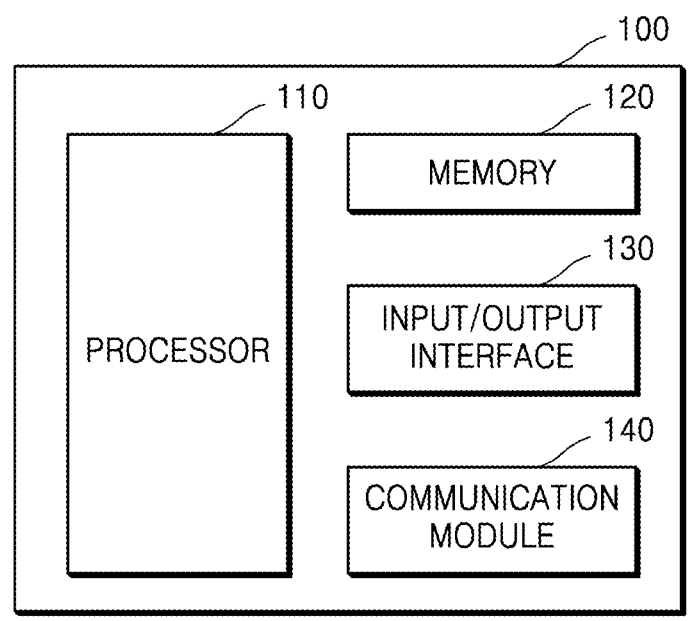
FIG. 3A is a block diagram illustrating an example of a user terminal according to an embodiment.

FIG. 3A is a block diagram illustrating an example of a user terminal according to an embodiment.

Referring to FIG. 3A, a user terminal 100 includes a processor 110, a memory 120, an input/output interface 130, and a communication module 140. For convenience of description, FIG. 3A illustrates only components related to the present disclosure. Accordingly, the user terminal 100 may further include other general-purpose components, in addition to the components illustrated in FIG. 3A. In addition, it is obvious to those of skill in the art related to the present disclosure that the processor 110, the memory 120, the input/output interface 130, and the communication module 140 illustrated in FIG. 3A may also be implemented as independent devices.

In addition, the operation of the user terminal 100 may be performed by the user terminals 11 and 12, the image management system 61, the AI-based biomarker analysis system 62, the laboratory information management system 63, and/or the hospital or laboratory server 70 of FIG. 2.

The processor 110 may process commands of a computer program by performing basic arithmetic, logic, and input/output operations. Here, the commands may be provided from the memory 120 or an external device (e.g., the server 20, etc.). In addition, the processor 110 may control the overall operation of other components included in the user terminal 100.

The processor 110 analyzes at least one object expressed in a pathological slide image. For example, the object may include a cell, a tissue, a structure, and the like. For example, the processor 110 may classify regions of the pathological slide image into at least one of a cancer region, a cancer stroma region, a necrosis region, and a background region. In addition, the processor 110 may classify a plurality of cells expressed in the pathological slide image into at least one of tumor cells, lymphocyte cells, and other cells.

In addition, the processor 110 evaluates the quality of the pathological slide image based on a result of analyzing the pathological slide image. For example, the processor 110 may perform, at least once, a first test by using at least one piece of quantitative information obtained from the pathological slide image. Thereafter, the processor 110 may perform a second test by using quantitative information of at least one biomarker expressed in the pathological slide image. Here, the second test may be performed on the pathological slide image that has passed the first test, but is not limited thereto.

The processor 110 may perform the first test for determining whether the pathological slide image passes quality evaluation, based on at least one of quantitative information corresponding to an analyzable region identified from the pathological slide image and quantitative information corresponding to a cancer region included in the pathological slide image. For example, the processor 110 may perform the first test by comparing at least one of the quantitative information corresponding to the analyzable region identified from the pathological slide image and the quantitative information corresponding to the cancer region included in the pathological slide image, with a preset reference value.

In addition, the processor 110 may perform the second test for determining whether the pathological slide image passes quality evaluation, based on quantitative information of at least one biomarker expressed in the pathological slide image. For example, the processor 110 may perform the second test by comparing the quantitative information of the at least one biomarker expressed in the pathological slide image, with a preset reference value. Here, the biomarker may include at least one of a tumor cell, a lymphocyte cell, and tumor purity.

In addition, the processor 110 performs at least one additional operation according to a result of the quality evaluation. For example, the processor 110 may control a display device to output at least one piece of information about the pathological slide image and the result of the quality evaluation. As another example, the processor 110 may control the display device to selectively output a result of analysis of the pathological slide image, according to the result of the quality evaluation. As another example, the processor 110 may generate a report including the result of the quality evaluation and a basis for the quality evaluation, and control the display device to output the report.

The processor 110 may be implemented as an array of a plurality of logic gates, or may be implemented as a combination of a general-purpose microprocessor and a memory storing a program executable by the microprocessor. For example, the processor 110 may include a general-purpose processor, a central processing unit (CPU), a microprocessor, a digital signal processor (DSP), a controller, a microcontroller, a state machine, etc. In some environments, the processor 110 may include an application-specific integrated circuit (ASIC), a programmable logic device (PLD), a field-programmable gate array (FPGA), etc. For example, processor 110 may refer to a combination of processing devices, such as a combination of a DSP and a microprocessor, a combination of a plurality of microprocessors, a combination of one or more microprocessors combined with a DSP core, or a combination of any other such configurations.

The memory 120 may include any non-transitory computer-readable recording medium. For example, the memory 120 may include a permanent mass storage device, such as random-access memory (RAM), read-only memory (ROM), a disk drive, a solid-state drive (SSD), or flash memory. As another example, the permanent mass storage device, such as ROM, an SSD, flash memory, or a disk drive, may be a permanent storage device separate from the memory. In addition, the memory 120 may store an operating system (OS) and at least one program code (e.g., code for the processor 110 to perform an operation to be described below with reference to FIGS. 4 to 11C).

These software components may be loaded from a computer-readable recording medium separate from the memory 120. The separate computer-readable recording medium may be a recording medium that may be directly connected to the user terminal 100, and may include, for example, a computer-readable recording medium, such as a floppy drive, a disk, a tape, a digital video disc (DVD)/compact disc ROM (CD-ROM) drive, or a memory card. Alternatively, the software components may be loaded into the memory 120 through the communication module 140 rather than a computer-readable recording medium. For example, at least one program may be loaded into the memory 120 on the basis of a computer program (e.g., a computer program for the processor 110 to perform an operation to be described below with reference to FIGS. 4 to 11C, or the like) installed by files provided via the communication module 140 by developers or a file distribution system that distributes installation files of applications.

The input/output interface 130 may be a unit for an interface with a device (e.g., a keyboard or a mouse) for input or output that may be connected to the user terminal 100 or included in the user terminal 100. Although FIG. 3A illustrates that the input/output interface 130 is an element implemented separately from the processor 110, the present disclosure is not limited thereto, and the input/output interface 130 may be implemented to be included in the processor 110.

The communication module 140 may provide a configuration or function for the server 20 and the user terminal 100 to communicate with each other through a network. In addition, the communication module 140 may provide a configuration or function for the user terminal 100 to communicate with another external device. For example, a control signal, a command, data, and the like provided under control by the processor 110 may be transmitted to the server 20 and/or an external device through the communication module 140 and a network.

Meanwhile, although not illustrated in FIG. 3A, the user terminal 100 may further include a display device. Alternatively, the user terminal 100 may be connected to an independent display device by a wired or wireless communication method to transmit and receive data to and from the display device. For example, a pathological slide image, information obtained by analyzing the pathological slide image, and therapeutic reaction prediction information may be provided to the user 30 through the display device.

Figure 3B:
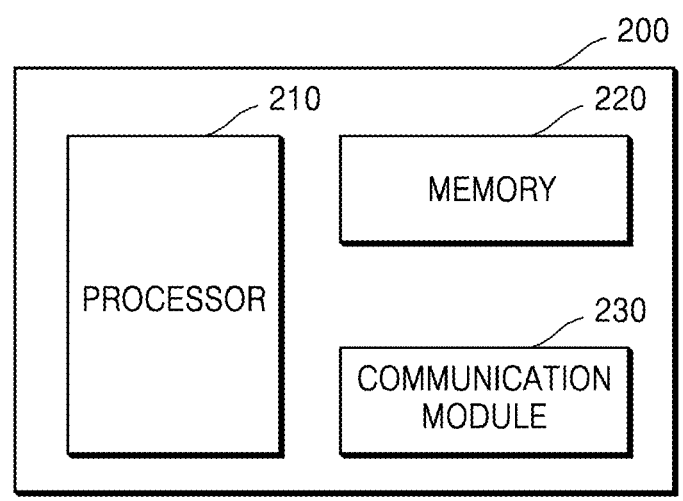
FIG. 3B is a configuration diagram illustrating an example of a server according to an embodiment.

FIG. 3B is a configuration diagram illustrating an example of a server according to an embodiment.

Referring to FIG. 3B, a server 200 includes a processor 210, a memory 220, and a communication module 230. For convenience of description, FIG. 3B illustrates only components related to the present disclosure. Accordingly, the server 200 may further include other general-purpose components, in addition to the components illustrated in FIG. 3B. In addition, it is obvious to those of skill in the art related to the present disclosure that the processor 210, the memory 220, and the communication module 230 illustrated in FIG. 3B may also be implemented as independent devices.

The processor 210 may obtain a pathological slide image from at least one of the memory 220, an external memory, the user terminal 100, and an external device. The processor 210 may analyze at least one object expressed in the pathological slide image, evaluate the quality of the pathological slide image based on a result of the analyzing, or perform at least one additional operation according to a result of the evaluating.

In other words, at least one of the operations of the processor 110 described above with reference to FIG. 3A may be performed by the processor 210. In this case, the user terminal 100 may output, through the display device, information transmitted from the server 200.

Meanwhile, an implementation example of the processor 210 is the same as that of the processor 110 described above with reference to FIG. 3A, and thus, detailed descriptions thereof will be omitted.

The memory 220 may store various pieces of data, such as a pathological slide image or data generated according to an operation of the processor 210. Also, the memory 220 may store an OS and at least one program (e.g., a program required for the processor 210 to operate, or the like).

Meanwhile, an implementation example of the memory 220 is the same as that of the memory 120 described above with reference to FIG. 3A, and thus, detailed descriptions thereof will be omitted.

The communication module 230 may provide a configuration or function for the server 200 and the user terminal 100 to communicate with each other through a network. In addition, the communication module 230 may provide a configuration or function for the server 200 to communicate with another external device. For example, a control signal, a command, data, and the like provided under control by the processor 210 may be transmitted to the user terminal 100 and/or an external device through the communication module 230 and a network.

Figure 4:
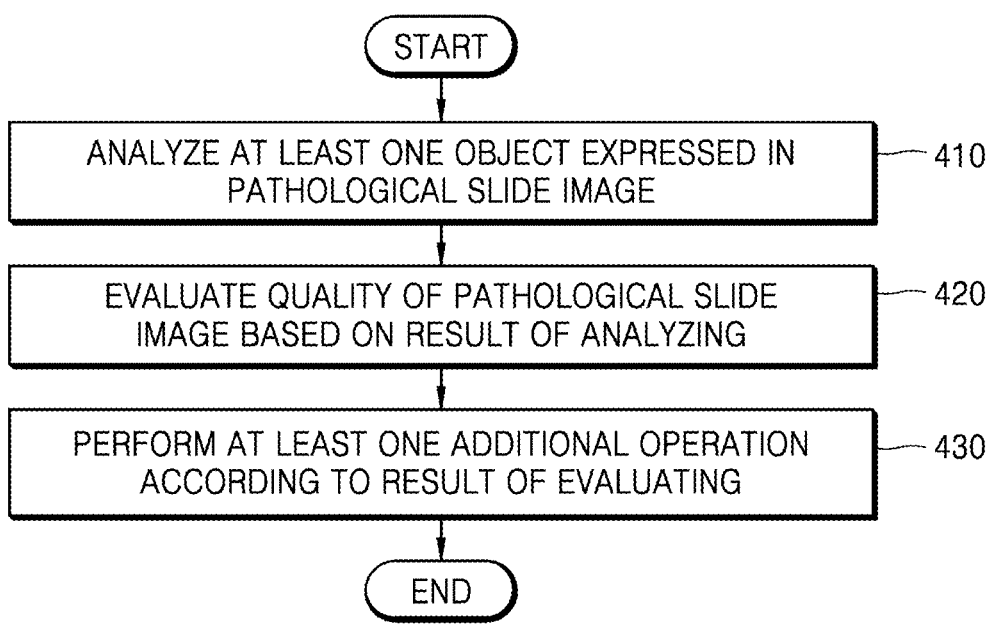
FIG. 4 is a flowchart illustrating an example of a method of analyzing a pathological slide image according to an embodiment.

FIG. 4 is a flowchart illustrating an example of a method of analyzing a pathological slide image according to an embodiment.

Referring to FIG. 4, the method of analyzing a pathological slide image includes operations that are processed, in a time-series manner, by the user terminal 10 or 100 or the processor 110 illustrated in FIGS. 1 to 3A. Thus, the descriptions provided above with respect to the user terminal 10 or 100 or the processor 110 illustrated in FIGS. 1 and 3A, which are even omitted below, may also be applied to the method of analyzing a pathological slide image of FIG. 4.

In addition, as described above with reference to FIGS. 1 to 3B, at least one of operations of the flowchart illustrated in FIG. 4 may be processed by the server 20 or 200 or the processor 210.

In operation 410, the processor 110 may analyze at least one object expressed in the pathological slide image. For example, the object may include a cell, a tissue, a structure, and the like.

For example, the processor 110 may classify regions on the pathological slide image into at least one of a cancer region, a cancer stroma region, a necrosis region, and a background region. In addition, the processor 110 may classify a plurality of cells expressed in the pathological slide image into at least one of tumor cells, lymphocyte cells, and other cells.

First, the processor 110 analyzes the pathological slide image. For example, the processor 110 may detect regions corresponding to tissues from the pathological slide image by analyzing the pathological slide image by using a predetermined image processing technique. The processor 110 may output a result of the detecting in the form of layers representing tissues. As another example, the processor 110 may detect regions corresponding to tissues from the pathological slide image by using a machine learning model. The processor 110 may output a result of the detecting in the form of layers representing tissues, by using the machine learning model. In this case, the machine learning model may be trained, by using training data including a plurality of reference pathological slide images and a plurality of pieces of reference label information, to detect regions corresponding to tissues in the reference pathological slide images.

Here, the machine learning model refers to a statistical learning algorithm implemented based on the structure of a biological neural network, or a structure for executing the algorithm, in machine learning technology and cognitive science.

For example, the machine learning model may refer to a machine learning model that obtains a problem-solving ability by repeatedly adjusting the weights of synapses by nodes that are artificial neurons forming a network by connection of the synapses as in biological neural network, to learn such that an error between a correct output corresponding to a particular input and an inferred output is reduced. For example, the machine learning model may include an arbitrary probability model, a neural network model, etc., used in AI learning methods, such as machine learning or deep learning.

For example, the machine learning model may be implemented as a multilayer perceptron (MLP) composed of multilayer nodes and connections therebetween. The machine learning model according to the present embodiment may be implemented by using one of various artificial neural network model structures including MLP. For example, the machine learning model may include an input layer that receives an input signal or data from the outside, an output layer that outputs an output signal or data corresponding to the input data, and at least one hidden layer between the input layer and the output layer to receive a signal from the input layer, extract features, and deliver the features to the output layer. The output layer receives a signal or data from the hidden layer and outputs the signal or data to the outside.

Thus, the machine learning model may be trained to receive one or more pathological slide images and extract features of one or more objects (e.g., cells, objects, structures, etc.) included in the pathological slide images.

In addition, the processor 110 may perform first classification on a plurality of tissues expressed in the pathological slide image. In detail, the processor 110 may classify regions of the pathological slide image into at least one of a cancer region, a cancer stroma region, a necrosis region, and a background region. Here, the background region may include a region representing biological noise and/or a region representing technical noise. For example, the region representing the biological noise may include a normal region, and the region representing the technical noise may include a degradation region.

However, examples in which the processor 110 classifies at least some regions expressed in a pathological slide image are not limited to the above description. In other words, without being limited to the above-described four types of regions (i.e., the cancer region, the cancer stroma region, the necrosis region, and the background region), the processor 110 may classify at least one region expressed in a pathological slide image into a plurality of categories according to various criteria. At least one region expressed in the pathological slide image may be classified into a plurality of categories according to a preset criterion or a criterion set by a user. In addition, the type of noise is not limited to biological noise and technical noise.

In addition, the processor 110 may perform second classification on a plurality of cells expressed in the pathological slide image, by analyzing the pathological slide image.

First, the processor 110 may analyze the pathological slide image to detect cells from the pathological slide image, and output a result of the detecting in the form of layers representing the cells. A detailed method of analyzing a pathological slide image by the processor 110 is the same as described above with respect to the first classification.

In addition, the processor 110 performs the second classification on the plurality of cells expressed in the pathological slide image. In detail, the processor 110 classifies cells expressed in the pathological slide image into at least one of tumor cells, lymphocyte cells, and other cells. However, an example in which the processor 110 classifies cells expressed in the pathological slide image is not limited to the above description. In other words, the processor 110 may group the cells expressed in the pathological slide image according to various criteria for classifying different types of cells.

Hereinafter, an example in which the processor 110 performs the first classification and the second classification on a plurality of tissues will be described with reference to FIGS. 5 and 6.

Figure 5:
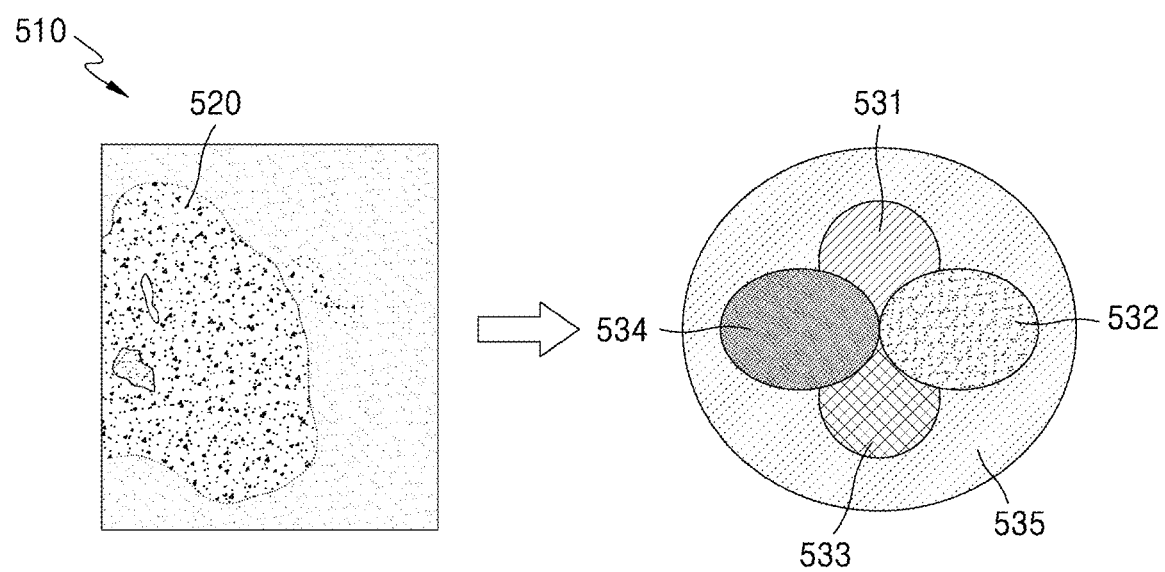
FIG. 5 is a diagram for describing an example in which a processor performs first classification on a plurality of tissues, according to an embodiment.

FIG. 5 is a diagram for describing an example in which a processor performs first classification on a plurality of tissues, according to an embodiment.

Referring to FIG. 5, the processor 110 may analyze a pathological slide image 510 to detect a region representing a tissue 520, and output a result of the detecting in the form of a layer representing the tissue 520. The tissue 520 of the pathological slide image 510 may include various regions 531 to 535, and the processor 110 may classify the regions 531 to 535. For example, the processor 110 may classify the regions 531 to 535 into the cancer region 531, the cancer stroma region 532, the necrosis region 533, the degradation region 534, and the normal region 535.

Figure 6:
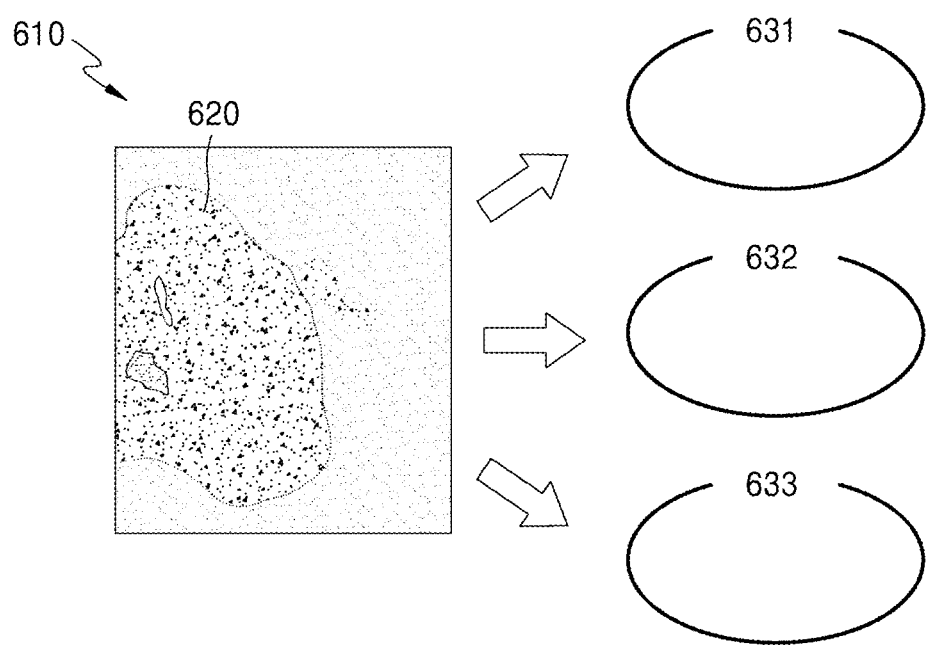
FIG. 6 is a diagram for describing an example in which a processor performs second classification on a plurality of cells, according to an embodiment.

FIG. 6 is a diagram for describing an example in which a processor performs second classification on a plurality of cells, according to an embodiment.

Referring to FIG. 6, the processor 110 analyzes a pathological slide image 610 to identify cells in a tissue 620. In detail, the processor 110 may detect a portion representing cells in the pathological slide image 610, and output a result of the detecting in the form of layers representing the cells.

The tissue 620 may be composed of a plurality of cells, and the cells may be of various types. The processor 110 may classify the cells into at least one of tumor cells 631, lymphocyte cells 632, and other cells 633. Here, the other cells 633 may include normal cells. For example, the other cells 633 may include at least one of epithelial cells, nerve cells, muscle cells, and connective tissue cells, but are not limited thereto.

According to the above descriptions with reference to operation 410 and FIGS. 5 and 6, the processor 110 may obtain information about tissues and cells in the pathological slide image. For example, the processor 110 may specify the positions of tissues and cells in the entire region of the pathological slide image. In addition, the processor 110 may identify the types of tissues and cells, and may obtain quantitative information by quantifying the number and density of cells included in each of the tissues. In addition, the processor 110 may accurately calculate tumor purity by using the quantitative information about the tissues and the cells.

In operation 420, the processor 110 evaluates the quality of the pathological slide image based on a result of the analyzing.

As described above with reference to operation 410, the processor 110 may obtain various pieces of quantitative information by analyzing the pathological slide image. In addition, the processor 110 may also calculate the tumor purity by using the quantitative information. Accordingly, the processor 110 may use, in a process of evaluating the pathological slide image, information derived by analyzing the pathological slide image.

For example, the processor 110 may perform, at least once, a first test by using at least one piece of quantitative information obtained from the pathological slide image. In addition, the processor 110 may perform a second test by using quantitative information of at least one biomarker expressed in the pathological slide image. Here, the second test may be performed on only the pathological slide image that has passed the first test, but is not limited thereto.

For example, the first test may include a process of comparing at least one of quantitative information corresponding to an analyzable region identified from the pathological slide image and quantitative information corresponding to a cancer region, with a preset reference value. In addition, the second test may include a process of comparing quantitative information of at least one biomarker expressed in the pathological slide image, with a preset reference value. Here, the at least one biomarker may include at least one of tumor cells, lymphocyte cells, and tumor purity.

Hereinafter, an example in which the processor 110 evaluates the quality of a pathological slide image will be described with reference to FIG. 7.

Figure 7:
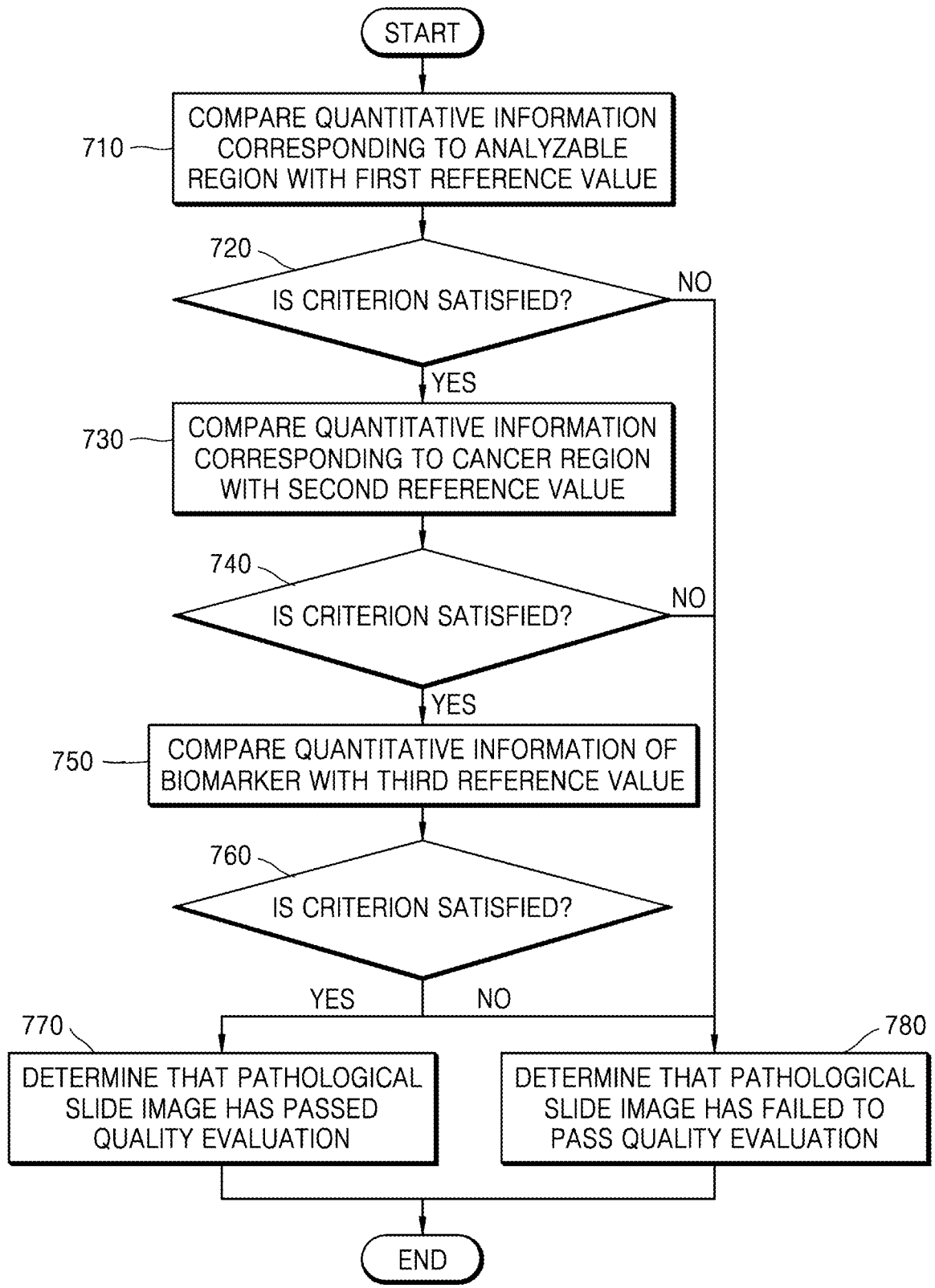
FIG. 7 is a flowchart for describing an example in which a processor evaluates the quality of a pathological slide image, according to an embodiment.

FIG. 7 is a flowchart for describing an example in which a processor evaluates the quality of a pathological slide image, according to an embodiment.

The flowchart illustrated in FIG. 7 includes a first test and a second test. For example, operations 710 to 740 may correspond to the first test, and operations 750 and 760 may correspond to the second test. In other words, the second test may be performed on only a pathological slide image that has passed the first test, and the first test may include at least one subtest.

However, the number of first tests and the condition for execution of the second test are not limited to those described above. In other words, the first test may include at least one of a first subtest (operations 710 and 720) and a second subtest (operations 730 and 740). In addition, the second test may be performed regardless of whether the pathological slide image passes the first test.

Through the first test and the second test, it may be determined whether the pathological slide image sufficiently includes content for a particular biomarker within an analyzable region of interest (ROI). In other words, the first test and the second test may be processes of determining whether a sufficient cancer region is expressed in the pathological slide image and/or whether various cells that may contribute to analyzing a biomarker are expressed. The pathological slide image that has passed the first test and the second test may move to the next process for downstream analysis.

The first test may be a test for determining whether a minimum requirement for the pathological slide image is satisfied. In other words, the processor 110 may determine whether the analyzable region and the cancer region of the pathological slide image satisfy the minimum criteria, through the first test.

In operation 710, the processor 110 compares quantitative information corresponding to the analyzable region, with a first reference value. The analyzable region is an entire region that may be analyzed in the pathological slide image, and may refer to an entire tissue region. According to a result of the analyzing in operation 410, the processor 110 may obtain quantitative information about the entire tissue region in the pathological slide image. For example, the quantitative information about the entire tissue region may include an area corresponding to a tissue region identified in the image. Accordingly, the processor 110 may compare the total sum of all tissue regions in the image, with the first reference value.

In operation 720, the processor 110 determines whether a result of the comparing between the total sum of the analyzable regions and the first reference value satisfies a predefined criterion. For example, the predefined criterion may be satisfied when the total sum of the analyzable regions is greater than or equal to the first reference value, but is not limited thereto. In a case in which the predefined criterion is satisfied, the process proceeds to operation 730, and when the predefined criterion is not satisfied, the process proceeds to operation 780.

In operation 730, the processor 110 compares the quantitative information corresponding to the cancer region, with a second reference value. According to a result of the analyzing in operation 410, the processor 110 may obtain the quantitative information about the cancer region in the pathological slide image. For example, the quantitative information about the cancer region may include an area corresponding to the cancer region identified in the image. Accordingly, the processor 110 may compare the total sum of cancer regions in the image, with the second reference value.

Alternatively, the processor 110 may compare the ratio of the analyzable region to the cancer region, with the second reference value. The analyzable region includes the cancer region. Accordingly, comparing the ratio of the cancer region to the analyzable region with the second reference value may achieve the same purpose as comparing the total sum of cancer regions in the image with the second reference value.

In operation 740, the processor 110 determines whether a result of the comparing between the total sum of cancer regions (or the ratio of the cancer region to the analyzable region) and the second reference value satisfies a predefined criterion. For example, the predefined criterion may be satisfied when the total sum of cancer regions (or the ratio of the cancer region to the analyzable region) is greater than or equal to the second reference value, but is not limited thereto. In a case in which the predefined criterion is satisfied, the process proceeds to operation 750, and when the predefined criterion is not satisfied, the process proceeds to operation 780.

The second test may be a test for determining whether the pathological slide image appropriately includes information about a particular biomarker. In other words, the processor 110 may determine whether information about a biomarker designated by the user 30 may be accurately identified from the pathological slide image, through the second test.

At least one biomarker may be expressed in the pathological slide image. Meanwhile, a biomarker of interest to the user 30 may vary and may be changed according to circumstances. Accordingly, the second test may be performed a plurality of times on a single pathological slide image, as the user 30 designates a particular biomarker.

In operation 750, the processor 110 compares quantitative information of a biomarker with a third reference value. Here, the biomarker may include at least one of proteins, DNA, RNA, metabolites, tumor cells, various types of cells such as lymphocyte cells, various phenotypes of tissues, and tumor purity. According to a result of the analyzing in operation 410, the processor 110 may obtain quantitative information about proteins, DNA, RNA, metabolites, or various cells in the pathological slide image. In addition, the processor 110 may calculate tumor purity based on information obtained through operation 410. Accordingly, the processor 110 may compare a quantitative information value of the biomarker designated by the user 30 with the third reference value.

In operation 760, the processor 110 determines whether a result of the comparing between the value of the biomarker and the third reference value satisfies a predefined criterion. For example, the defined criterion may be satisfied when the value of the biomarker is greater than or equal to the third reference value, but is not limited thereto. In a case in which the predefined criterion is satisfied, the process proceeds to operation 770, and when the predefined criterion is not satisfied, the process proceeds to operation 780.

In operation 770, the processor 110 may determine that the pathological slide image has passed the quality evaluation. In addition, in operation 780, the processor 110 may determine that the pathological slide image has failed to pass the quality evaluation.

Meanwhile, the above-described reference values (i.e., the first reference value, the second reference value, and the third reference value) may be determined based on various criteria. For example, the reference values may be variously determined according to a setting by the user 30, the type of pathological slide image, the type of target cancer, functional requirements of a biomarker, a disease state, or research on clinical validation.

For example, the reference values may be determined considering a minimum value of The Cancer Genome Atlas (TCGA) slide image.

For example, the reference values may be determined considering functional requirements of a biomarker. The functional requirements of a biomarker may refer to requirements that need to be satisfied under the premise that the biomarker needs to be accurately identifiable and measurable, and provide useful information for diagnosis, prediction, or treatment of a particular disease or condition. The functional requirements of a biomarker may include functional requirements such as sensitivity, specificity, a positive predictive value (ppv), a negative predictive value (npv), safety, non-invasiveness, or reproducibility. For example, the cobas epidermal growth factor receptor (EGFR) Mutation Test may be an example that satisfies the functional requirements of a biomarker. The functional requirements of a biomarker may be determined with reference to the FDA's Biomarkers and qualification link (https://www.fda.gov/drugs/biomarker-qualification-program/about-biomarkers-and-qualification) and Biomarker qualification submission list (https://www.fda.gov/drugs/biomarker-qualification-program/biomarker-qualification-submissions).

For example, assuming that tumor-infiltrating lymphocytes are measured through a pathological slide image, an immunophenotype classification process is performed in a case in which the proportion of lymphocytes in a cancer region or a cancer stroma region is greater than the reference value. In addition, in a case in which the proportion of tumor cells in a cancer region is greater than a reference value, an immunophenotype classification process is performed. Therefore, when the proportion of lymphocytes or tumor cells in a cancer region or a cancer stroma region does not satisfy the reference value, it is classified as an unknown immune phenotype and does not pass the image quality evaluation.

In addition, a reference value of a biomarker may vary depending on an index to be measured based on the biomarker. For example, in a case of tumor purity, a reference value for passing image quality evaluation may be determined as low as 1 or 0. Similarly, calculation of a PD-L1 tumor proportion score (TPS) may be determined as low as 1 or 0 relative to the number of viable tumor cells.

Referring back to FIG. 4, in operation 430, the processor 110 performs at least one additional operation according to a result of the evaluating.

For example, the processor 110 may display at least one piece of information about the pathological slide image and the result of evaluating in operation 420 together. For example, the processor 110 may display the above-described content by controlling the display device. An example in which the processor 110 displays at least one piece of information about a pathological slide image and a result of evaluation will be described below with reference to FIG. 8.

As another example, the processor 110 may selectively display the result of the analyzing in operation 410 according to the result of the evaluating in operation 420. For example, the processor 110 may display the above-described content by controlling the display device. An example in which the processor 110 selectively displays a result of analysis according to a result of evaluation will be described below with reference to FIG. 9.

As another example, the processor 110 may generate a report including the result of the evaluating in operation 420 and the basis of the evaluating. Then, the processor 110 may control the display device to display the report. An example of a report generated by the processor 110 will be described below with reference to FIG. 10.

Figure 8:
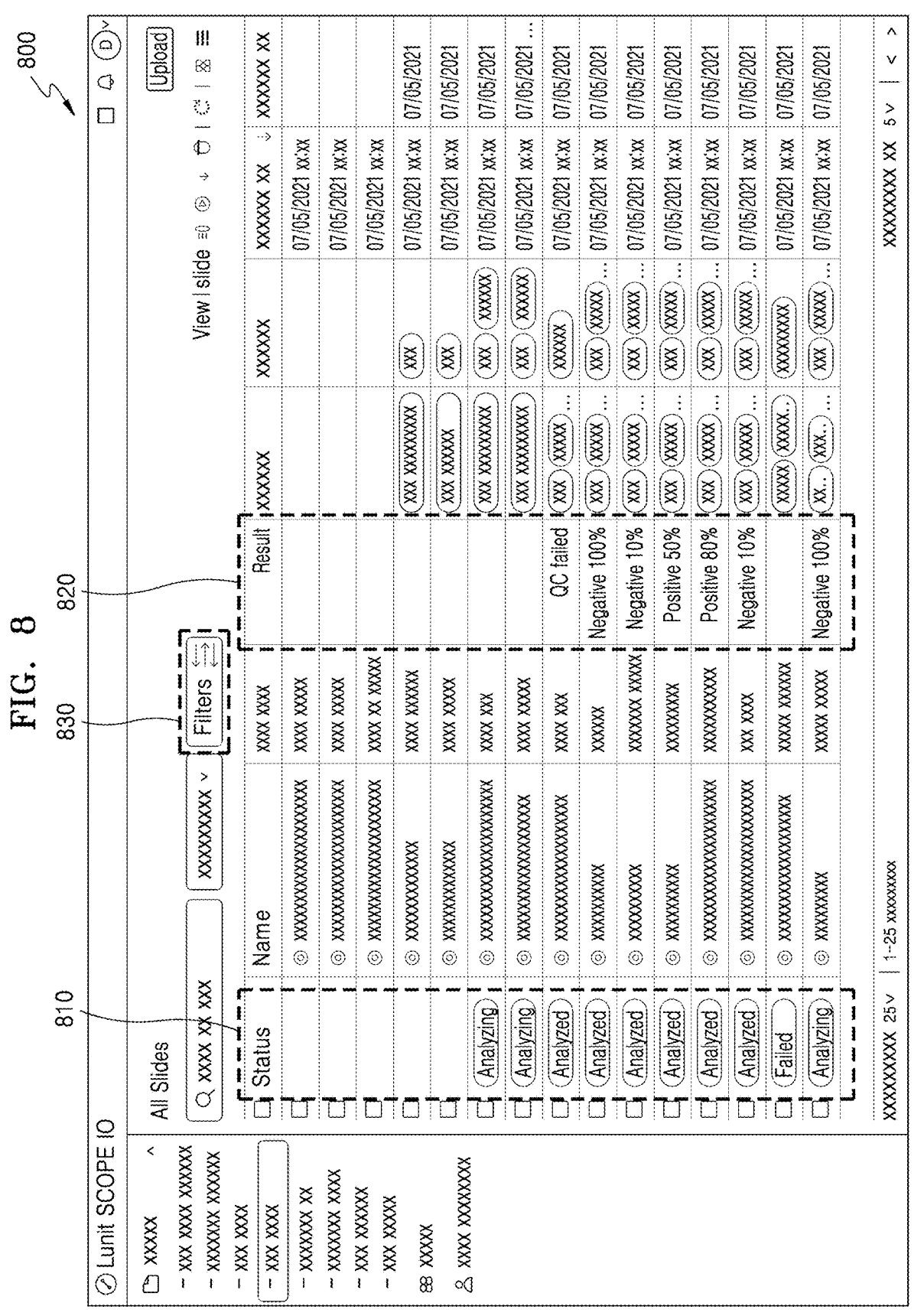

FIG. 8 is a diagram illustrating an example of a screen displayed by a processor according to an embodiment.

FIG. 8 illustrates an example of an execution screen 800 of a program by which the method described above with reference to FIGS. 1 to 7 is executed. At least one piece of information about a pathological slide image and the result of the evaluating in operation 420 may be displayed together on the execution screen 800.

For example, the current state of analysis or quality evaluation of the pathological slide image may be displayed in a region 810. In detail, 'upload' may be output when the analysis or quality evaluation is not yet performed, 'analyzing' may be output when the analysis or quality evaluation is in progress, 'analyzed' may be output when the analysis or quality evaluation is completed, 'failed' may be output when an error occurs in the analysis or quality evaluation.

In addition, a result of the analysis or quality evaluation of the pathological slide image may be displayed in a region 820. In detail, 'QC failed' may be displayed in a case in which the pathological slide image has failed to pass the quality evaluation, and a result of analysis may be schematically displayed in a case in which the pathological slide image has passed the quality evaluation.

In addition, an indicator for designating filters of various conditions may be displayed in a region 830. Thus, the user 30 may select only desired information by using the indicator, and the configuration of the execution screen 800 may be changed based on the selected information.

Figure 9:
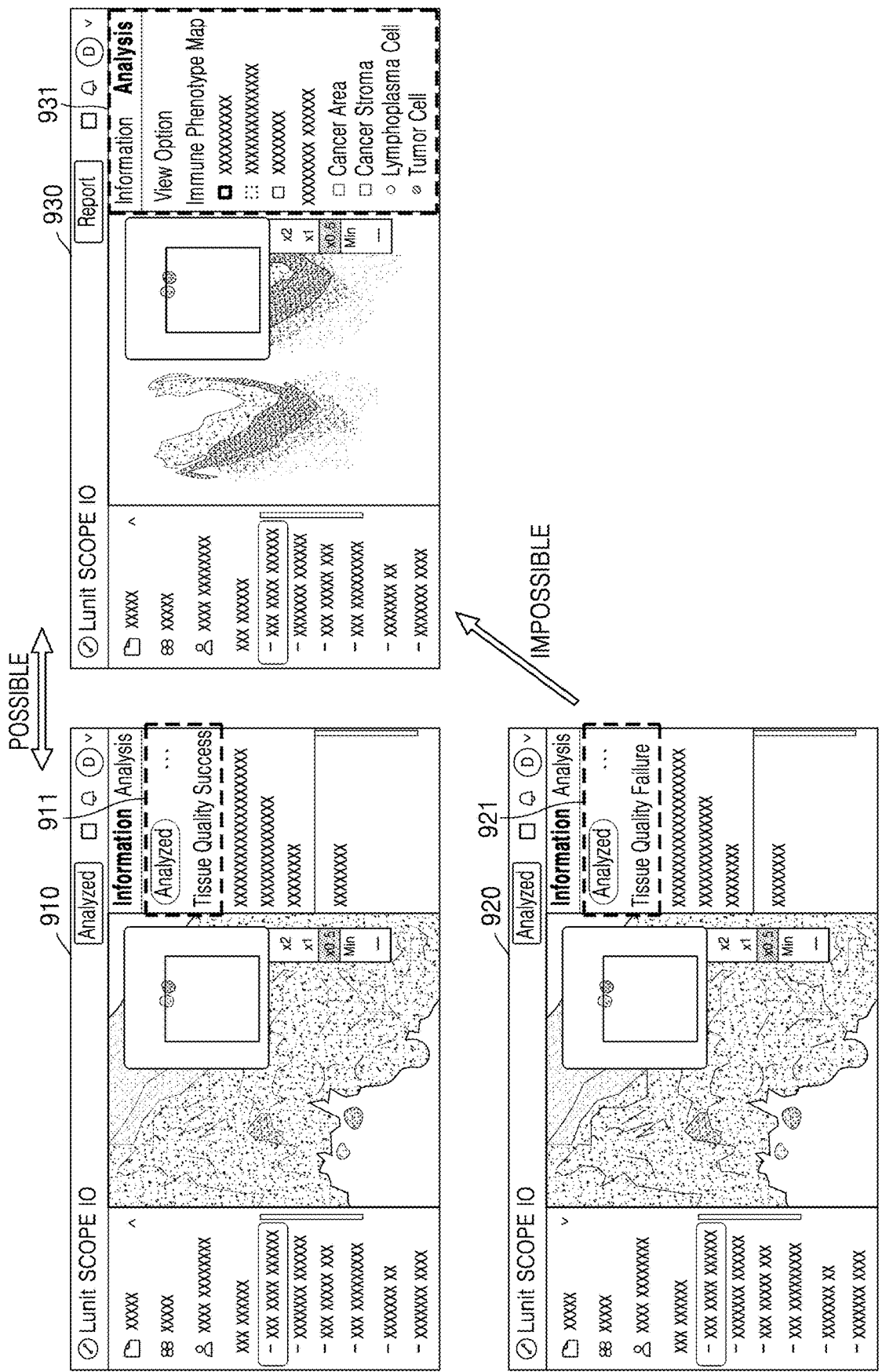
FIG. 9 is a diagram illustrating another example of a screen displayed by a processor according to an embodiment.

FIG. 9 is a diagram illustrating another example of a screen displayed by a processor according to an embodiment.

FIG. 9 illustrates execution screens 910, 920, and 930 for describing an example of selectively displaying a result of analysis according to a result of quality evaluation of a pathological slide image.

For example, in a case in which the pathological slide image has passed quality evaluation, a text, an image, etc. indicating that the analysis has been completed and the pathological slide image has passed the quality evaluation may be displayed in one region 911 of the screen 910. The screen 910 may represent an example of an information viewer. When the screen 910 is manipulated by the user 30, the screen 910 may be changed to another screen 930. The screen 930 may represent an example of an analysis viewer. Here, a result of analysis of the pathological slide image may be output on one region 931 of the screen 930.

Meanwhile, in a case in which the pathological slide image has failed to pass the quality evaluation, a text, an image, etc. indicating that the analysis has been completed and the pathological slide image has failed to pass the quality evaluation may be displayed in one region 921 of the screen 920. The screen 930 may represent an example of an analysis viewer. Here, even when the user 30 performs a manipulation to change the screen 920 to the other screen 930, the screen 930 may not be output. In other words, when the pathological slide image has failed to pass the quality evaluation, the result of analysis of the image may not be output.

Figure 10:
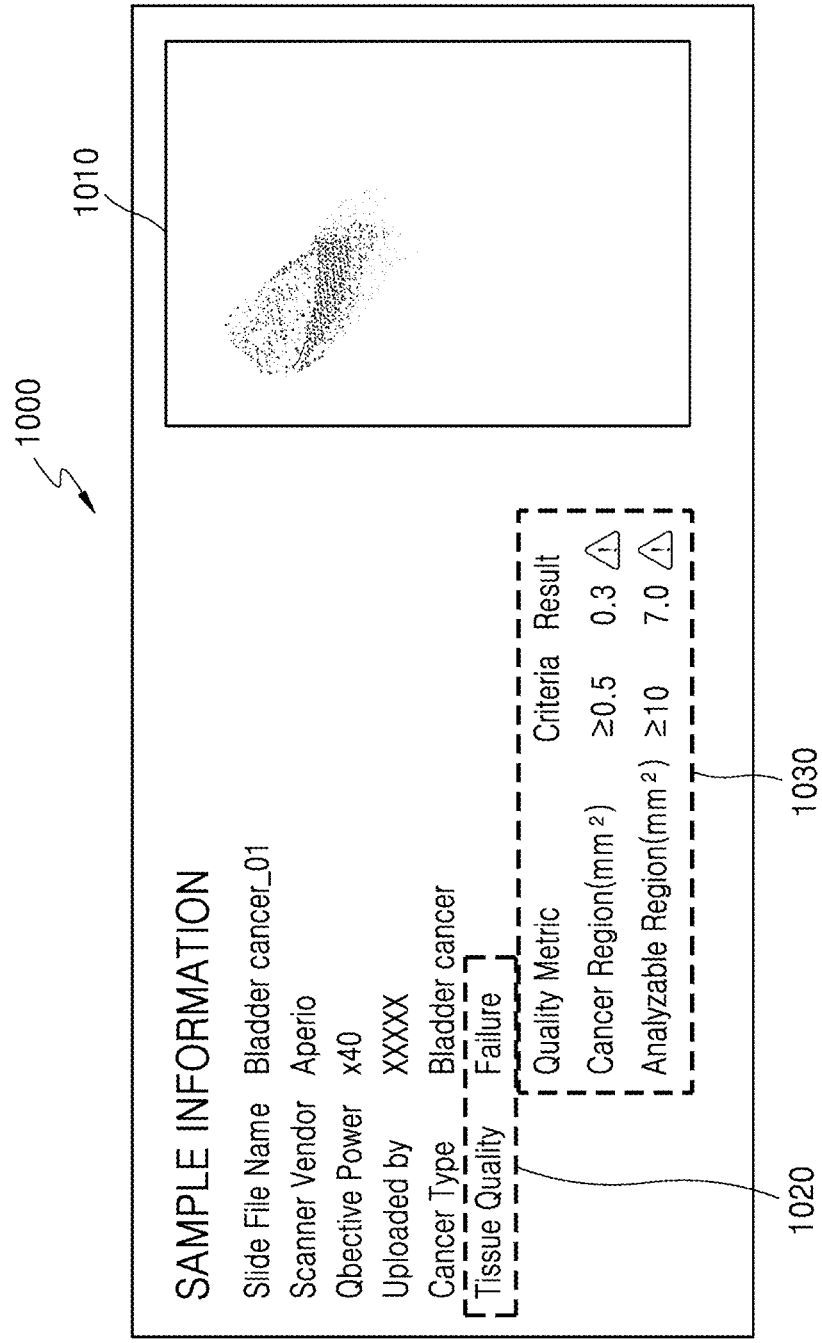
FIG. 10 is a diagram illustrating an example of a report according to an embodiment.

FIG. 10 is a diagram illustrating an example of a report according to an embodiment.

A report 1000 may include a thumbnail 1010 of a pathological slide image and various pieces of information about the pathological slide image. For example, the report 1000 may include the name, magnification, cancer type, and the like of the pathological slide image.

In addition, the report 1000 may include a result 1020 of quality evaluation of the pathological slide image and a basis 1030 of deriving the result 1020. For example, in a case in which the image has failed to pass the quality evaluation, criteria of a first test and/or a second test and quantitative information obtained from the image may be output together. Accordingly, the user 30 may check a quality result of the image and the basis thereof together.

Meanwhile, through the execution screen 800 described above with reference to FIG. 8, the user 30 may generate/modify/delete information about the pathological slide image. Hereinafter, an example of generating/modifying/deleting information will be described with reference to FIGS. 11A to 11C.

Figure 11A:
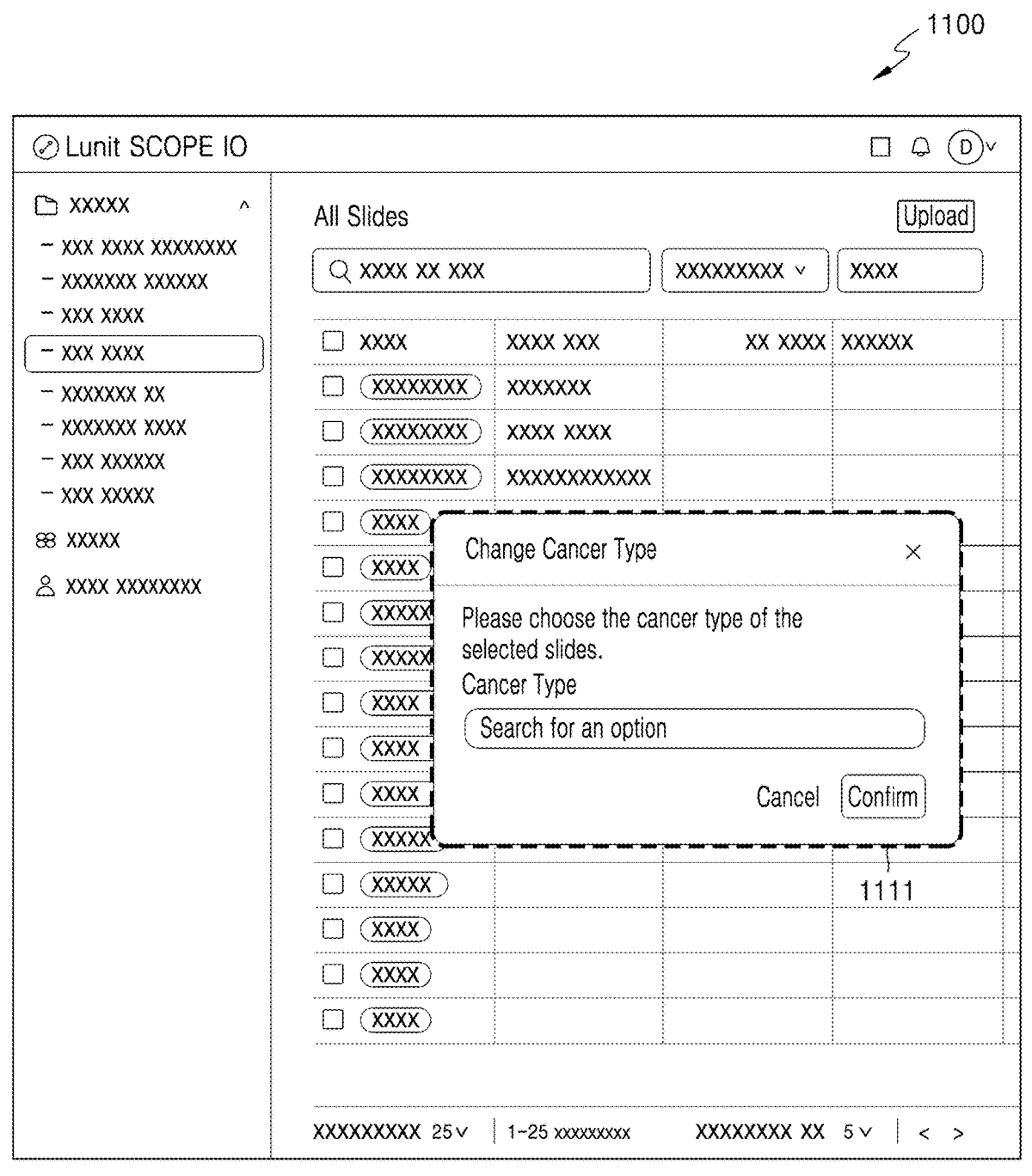
Figure 11B:
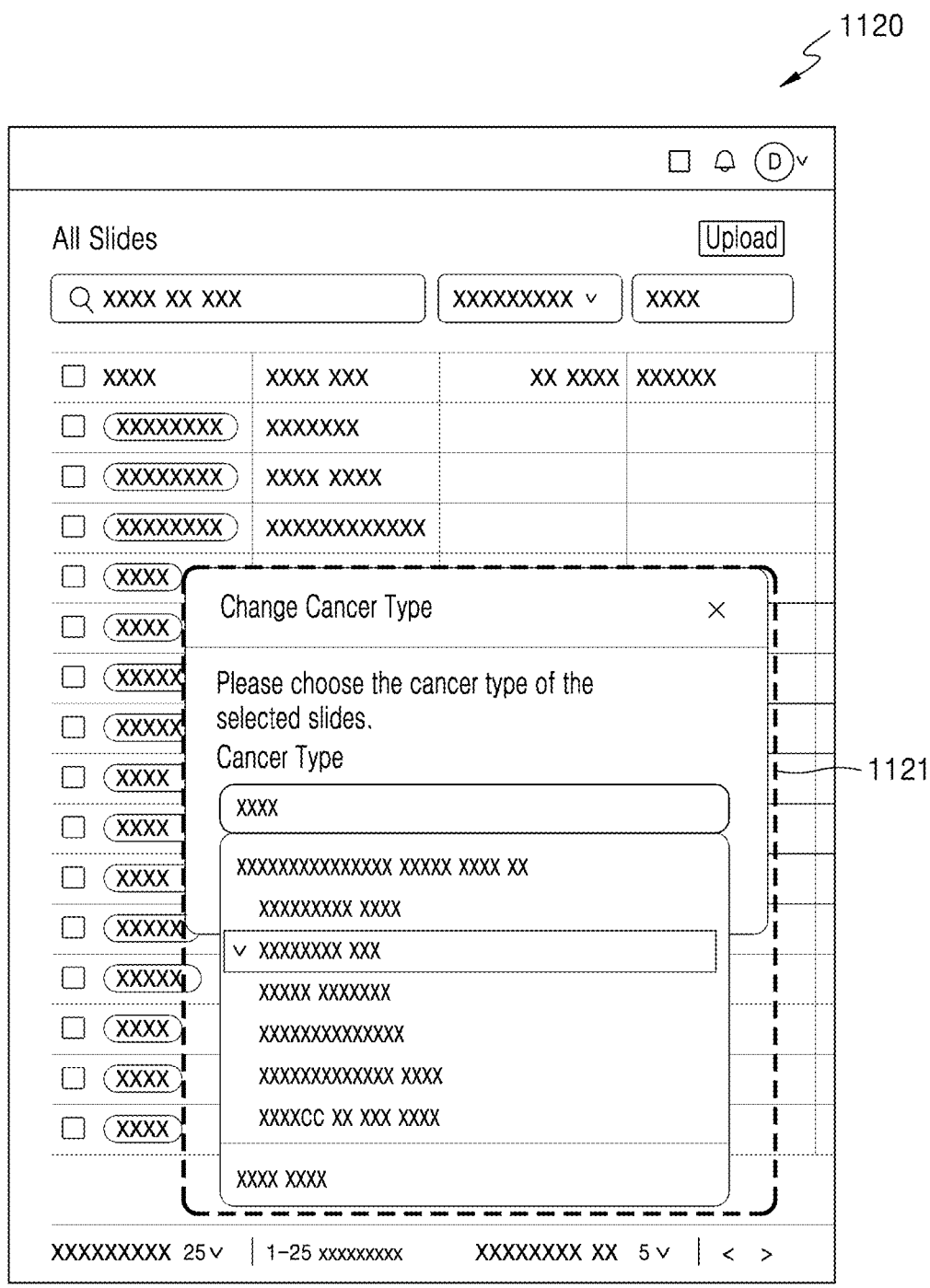
Figure 11C:
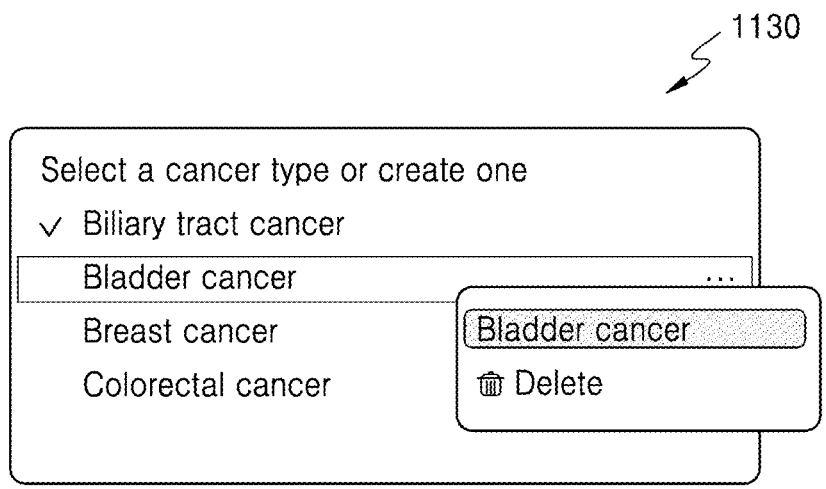

FIGS. 11A to 11C are diagrams for describing examples of modifying information related to a pathological slide image, according to an embodiment.

Referring to FIG. 11A, the user 30 may modify information about a pathological slide image in a list output on a screen 1100. For example, the user 30 may modify preset information (e.g., the type of the pathological slide image, the type of cancer, the type of a biomarker, a disease state, etc.) through a window 1111. Here, the window 1111 may be output according to a selection of a certain indicator in the screen 1100 by the user 30. As the information about the pathological slide image is modified, the processor 110 may modify a criterion of quality evaluation of the pathological slide image. For example, as the information about the pathological slide image is modified, the processor 110 may modify a target for obtaining quantitative information, which is a basis for the quality evaluation. Alternatively, as the information about the pathological slide image is modified, the processor 110 may modify a reference value applied to determine whether the pathological slide image passes the quality evaluation.

Referring to FIG. 11B, the user 30 may generate information about a pathological slide image in a list output on a screen 1120. For example, the user 30 may newly generate certain information (e.g., the type of cancer) through a window 1121. Here, the window 1121 may be output according to a selection of a certain indicator in the screen 1120 by the user 30.

Referring to FIG. 11C, the user 30 may delete preset information (e.g., the type of cancer) through a window 1130. Here, the window 1130 may be output according to a selection of a certain indicator in the screen 1100 or 1120 by the user 30.

According to the above descriptions, the user 30 may check a result of quality evaluation of a pathological slide image, and the accuracy of downstream analysis of the pathological slide image may be improved. Furthermore, an evaluation method according to an embodiment may be provided as a standard method for managing the quality of a pathological slide image, and standardization of machine learning models for workflows of digital pathology may be established.

Meanwhile, the above-described method may be written as a computer-executable program, and may be implemented in a general-purpose digital computer that executes the program by using a computer-readable recording medium. In addition, the structure of the data used in the above-described method may be recorded in a computer-readable recording medium through various units. The computer-readable recording medium includes a storage medium, such as a magnetic storage medium (e.g., ROM, RAM, a universal serial bus (USB) drive, a floppy disk, a hard disk, etc.) and an optically readable medium (e.g., a CD-ROM, a DVD, etc.).

It will be understood by those of skill in the art that the present disclosure may be implemented in a modified form without departing from the intrinsic characteristics of the descriptions provided above. Therefore, the disclosed methods should be considered in an illustrative rather than a restrictive sense, and the scope of the present disclosure should be defined by claims rather than the foregoing description, and should be construed to include all differences within the scope equivalent thereto.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A computing device comprising:
   at least one memory; and
   at least one processor configured to:
   use a machine learning model to detect a plurality of tissue regions and cancer region from a pathological slide image,
   generate quantitative information about the detected tissue regions and cancer region,
   compare the quantitative information with a predetermined reference value, wherein the quantitative information comprises an area corresponding to entire tissue regions and an area corresponding to the cancer region,
   determine whether the pathological slide image has passed a quality evaluation test based on a comparison between the quantitative information with the predetermined reference value, such that a result of the quality evaluation test is used in determining whether to perform downstream analysis on the pathological slide image, and
   display on a display device the result of the quality evaluation test indicating whether the pathological slide image has passed the quality evaluation test,
   wherein the processor determines that the pathological slide image has failed the quality evaluation test if the area corresponding to entire tissue regions is smaller than a first reference value or the area corresponding to the cancer region is smaller than a second reference value.

2. The computing device of claim 1, wherein the at least one processor is further configured to:
compare quantitative information of a biomarker with a third reference value,
wherein the quantitative information of the biomarker is comprised of the obtained quantitative information.

3. The computing device of claim 2, wherein the at least one processor is configured to:
compare the quantitative information of the biomarker with the third reference value if the area corresponding to the entire tissue regions exceeds the first reference value and the area corresponding to the cancer region exceeds the second reference value.

4. The computing device of claim 2, wherein the quantitative information of the biomarker is related to at least one of a tumor cell, a lymphocyte cell, and tumor purity.

5. The computing device of claim 1, wherein the at least one processor is further configured to obtain information about the at least one of the tissue regions, the cancer region, a the biomarker by analyzing the pathological slide image with the machine learning model, and control the display device to selectively display the information with the pathological slide image based on the result of the quality evaluation test.

6. The computing device of claim 5, wherein the at least one processor is further configured to control the display device to display the pathological slide image without the information if the pathological slide image has failed the quality evaluation test.

7. The computing device of claim 1, wherein the at least one processor is further configured to generate a report comprising the result of the quality evaluation test and a basis of the result.

8. The computing device of claim 1, wherein the at least one processor is further configured to classify regions of the pathological slide image into at least one of the cancer region, a cancer stroma region, a necrosis region, and a background region, and classify a plurality of cells expressed in the pathological slide image into at least one of tumor cells, lymphocyte cells, and other cells.

9. A method of evaluating a pathological slide image, the method comprising:
using a machine learning model to detect a plurality of tissue regions and cancer region from a pathological slide image;
generating quantitative information about the detected tissue regions and cancer region;
comparing the quantitative information with a predetermined reference value, wherein the quantitative information comprises an area corresponding to entire tissue regions and an area corresponding to the cancer region;
determining whether the pathological slide image has passed a quality evaluation test based on a comparison between the quantitative information with the predetermined reference value, such that a result of the quality evaluation test is used in determining whether to perform downstream analysis on the pathological slide image; and
displaying on a display device the result of the quality evaluation test indicating whether the pathological slide image has passed the quality evaluation test,
wherein the determining comprises determining that the pathological slide image has failed the quality evaluation test if the area corresponding to entire tissue regions is smaller than a first reference value or the area corresponding to the cancer region is smaller than a second reference value.

10. The method of claim 9, wherein the determining comprises:
comparing quantitative information of a biomarker with a third reference value,
wherein the quantitative information of the biomarker is comprised of the obtained quantitative information.

11. The method of claim 10, wherein comparing the quantitative information of the biomarker with the third reference value comprises comparing the quantitative information of the biomarker with the third reference value if the area corresponding to the entire tissue regions exceeds the first reference value and the area corresponding to the cancer region exceeds the second reference value.

12. The method of claim 10, wherein the quantitative information of the biomarker is related to at least one of a tumor cell, a lymphocyte cell, and tumor purity.

13. The method of claim 9, further comprises obtaining information about the at least one of the tissue regions, the cancer region, and a biomarker by analyzing the pathological slide image with the machine learning model,
wherein the performing of the at least one additional operation comprises selectively displaying the information with the pathological slide image based on the result of the quality evaluation test.

14. The method of claim 13, wherein the performing of the at least one additional operation comprises displaying the pathological slide image without the information if the pathological slide image has failed the quality evaluation test.

15. The method of claim 9, wherein the performing of the at least one additional operation comprises generating a report comprising the result of the quality evaluation test and a basis of the result.

16. The method of claim 9, wherein the analyzing comprises:
classifying regions of the pathological slide image into at least one of the cancer region, a cancer stroma region, a necrosis region, and a background region; and
classifying a plurality of cells expressed in the pathological slide image into at least one of tumor cells, lymphocyte cells, and other cells.

17. A non-transitory computer-readable recording medium having recorded thereon a program for causing a computer to execute the method of claim 9.

* * * * *